United States Patent [19]

Kitajima

[11] Patent Number: 5,249,004
[45] Date of Patent: Sep. 28, 1993

[54] MICROSCOPE FOR AN OPERATION
[75] Inventor: Nobuaki Kitajima, Tokyo, Japan
[73] Assignee: Kabushiki Kaisha Topcon, Tokyo, Japan
[21] Appl. No.: 934,907
[22] Filed: Aug. 26, 1992

Related U.S. Application Data

[63] Continuation of Ser. No. 633,359, Dec. 28, 1990, abandoned.

[30] Foreign Application Priority Data

Dec. 28, 1989 [JP] Japan .................................. 1-344028

[51] Int. Cl.$^5$ ............................................. A61B 3/10
[52] U.S. Cl. .................................. 351/211; 351/205; 351/206
[58] Field of Search ............... 351/205, 206, 211, 207, 351/208; 606/4, 5, 6

[56] References Cited

U.S. PATENT DOCUMENTS 4,917,480  4/1990  Kato et al. ......................... 351/211

Primary Examiner—Bruce Y. Arnold
Assistant Examiner—Hung X. Dang
Attorney, Agent, or Firm—Finnegan, Henderson, Farabow, Garrett & Dunner

[57] ABSTRACT

A microscope for an operation for measuring the refraction of an eye. The microscope has a measuring device for measuring the refraction of an eye to be tested and can achieve its miniaturization by sharing a part of the optical axes among the illuminating optical system, the projecting optical system, and the receiving optical system.

8 Claims, 5 Drawing Sheets

F I G. 1
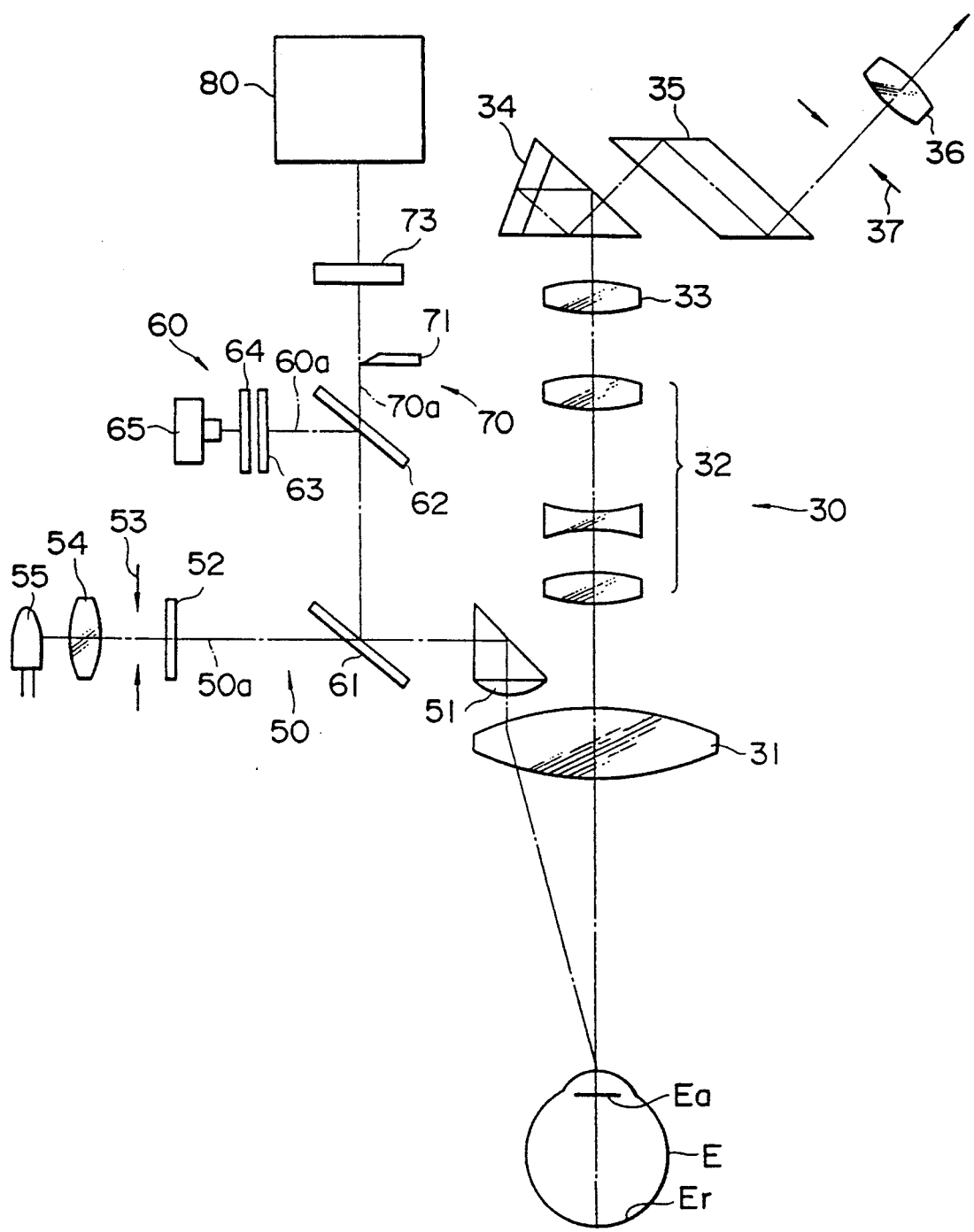

PRIOR ART

PRIOR ART

MICROSCOPE FOR AN OPERATION

This application is a continuation of application Ser. No. 07/633,359, filed Dec. 28, 1990, now abandoned.

BACKGROUND OF THE INVENTION

The present invention relates to a microscope for an operation for measuring the refraction of an eye.

PRIOR ART OF THE INVENTION

Heretofore a microscope such as in FIG. 6 is known. Referring to FIG. 6, light emitted from a lamp 1 illuminates the front portion of an eye to be tested through a half mirror 2, a condenser lens 3, a lens with a prism 4, and an objective lens 5. Light reflected on the front portion passes through the objective lens 5, a half mirror 14, a variable power system 6, mirrors 9, 10, and finally it is observed by an observer through an eyepiece 11. The numerals 12 and 13 in FIG. 6 designate a film and a storoboscope, respectively. And the numeral 20 is a light source for illuminating a light projecting chart 18 having three slits, as shown in detail in FIG. 7, via a lens 19. Fluxes of light through each slit 18a, 18b, 18c are projected onto an fundus Er of an eye to be tested E via a relay lens 17, a half mirror 16, a relay lens 15, a half mirror 14, and an objective lens 5. The reflection light reflected on the fundus Er is projected onto a light receiving chart 22 conjugated with the light projecting chart 18 via the objective lens 5, the half mirror 14, the relay lens 15, the half mirror 16, and a relay lens 21. Light for forming an image through each slit 18a, 18b, 18c of the light projecting chart 18 is detected by light receiving elements 23a, 23b, 23c corresponding to each slit 22a, 22b, 22c through the slits of the light receiving chart 22 in FIG. 8.

And then the half mirror 14 is moved along the optical axis O together with an eye-refraction meter 24, and the positions for the best focused image for each slit are detected based on each output of the light receiving elements 23a, 23b, 23c. The refraction of an eye to be tested corresponding to each slit direction is obtained based on the moving amount from the starting point of the eye refraction meter 24 to the point for the best focused image, and consequently the spherical refractive index S, the astigmatic index C. and the angle of the axis of the astigmatism A are calculated. In other words, the refraction of an eye to be tested can be determined based on the fact that the output of the light receiving element is highest in the case of a conjugate position of the light projecting chart 18 and the light receiving chart 22 relative to the fundus.

Therefore, since the refraction of an eye to be tested is obtained during the operation with the above-mentioned microscope, an operator can carry out it while checking the condition of an eye to be tested. However, the such known microscopes have a disadvantage in that they are large in size and therefore present an obstruction to the operators and physicians carrying out the operation, primarily because its construction is simply the addition of a refractometer to a microscope.

SUMMARY OF THE INVENTION

An object of the present invention is to provide a small-sized microscope for an operation. This invention is characterized in that a measuring means for measuring the refraction of an eye to be tested is disposed based on the distribution of the quantity of light projected onto a light receiving element and there is a common part of the optical axes among the illuminating optical system, the optical system for projecting fluxes of light for measurement (hereinafter referred to as the projecting optical system, for brevity), and the light receiving optical system.

BRIEF DESCRIPTION OF THE DRAWINGS

FIG. 1 is a schematic view showing the construction of the optical system of a microscope for an operation according to the invention.

DETAILED DESCRIPTION

Figure 2:
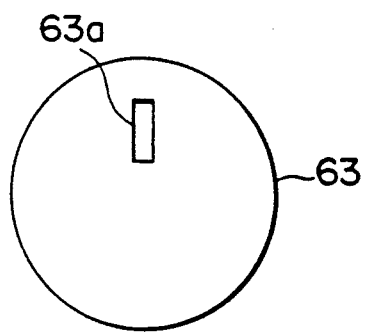
FIG. 2 is a plan view showing a slit plate.

The embodiment of the present invention will be hereinafter described with reference to the drawings.

Referring now to FIG. 1, a microscope for an operation comprises an observing optical system 30 for observing an fundus Er of an eye E to be tested through an objective lens 31, an illuminating optical system 50 for illuminating the fundus Er through the objective lens 31, a projecting optical system 60 for projecting measuring fluxes onto the fundus Er through the objective lens 31, and a light receiving optical system 70 for receiving the reflection fluxes of light of the measuring fluxes reflected on the fundus Er.

The observing optical system 30 comprises a zoom lens 32, an image-formation lens 33, an erect prism 34, a prism 35, an eyepiece 36, and a diaphragm 37.

The illuminating optical system 50 comprises a lens with a prism 51, a filter 52 for transmission of visible light, a diaphragm 53 for illumination, a condenser lens 54, and a light source 55.

The projecting optical system 60 comprises a lens with a prism 51, a dichroic mirror 61, a half mirror 62, a slit plate 63 conjugated with the fundus Er of the eye E having a normal refraction, a diffusion plate 64, and a light emitting diode 65 for emitting infrared rays. The optical axis 60a of the projecting optical system 60 is partially common to the axis 50a of the illuminating optical system 50. The slit plate has a slit aperture 63a functioning as a surface light source as shown in FIG. 2.

The light receiving optical system 70 comprises a lens with a prism 51, a dichroic mirror 61, a shade member 71 conjugated with the slit plate 63, and a light receiving element 73 conjugated with a pupil Ea. The axis of the light receiving optical system 70 is partially common to the axis 70a of the projecting optical system.

Figure 3:
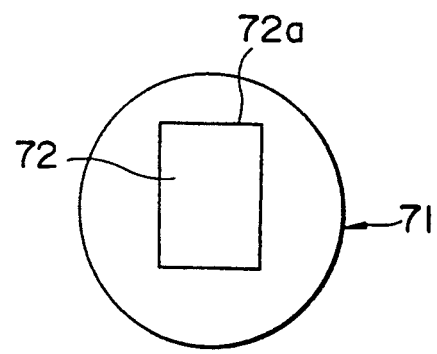
FIG. 3 is a plan view showing a shade member.

The shade member 71 has an transmission aperture 72 having an edge 72a perpendicular to a longitudinal line of the slit aperture 63a of the slit plate 63 as shown in FIG. 3.

The numeral 80 designates a measuring means for calculating the refraction of an eye to be tested from the distribution of the quantity of light on a light receiving element 73.

Next, there will be described the function of a microscope for an operation in the above-mentioned embodiment.

In FIG. 1, illuminating light emitted from the light source 55 illuminates the eye E via a condenser lens 54, a diaphragm 53 for illumination, a filter 52 for transmitting visible light, a dichroic mirror 61, a lens with a prism 51, and an objective lens 31. The reflection fluxes of light reflected on the eye E reach the observer's eye (not shown) for observing the front portion of the eye E via the objective lens 31, a zoom lens 32, an image-formation lens 33, prisms 34, 35, and an eyepiece 36.

Infrared rays are emitted from the light emitting diode 65 to measure the eye-refraction. The infrared rays from the diode 65 are projected onto the fundus Er of the eye E via the diffusion plate 64, the slit aperture 63a of a slit plate 63, the half mirror 62, the dichroic mirror 61, the lens with a prism 51, and the objective lens 31. In other words, a slit image through the slit aperture 63a is projected onto the fundus Er. The infrared rays for forming the slit image are reflected on the fundus Er and then reach the light receiving element 73 via the objective lens 31, the lens with a prism 51, the dichroic mirror 61, the half mirror 62, and the shade member 71.

Next, there will be described the relation between the refraction of the eye E and the distribution of the quantity of light of the light receiving element 73 with reference to FIGS. 4(a) through 4(c).

Figure 4A:
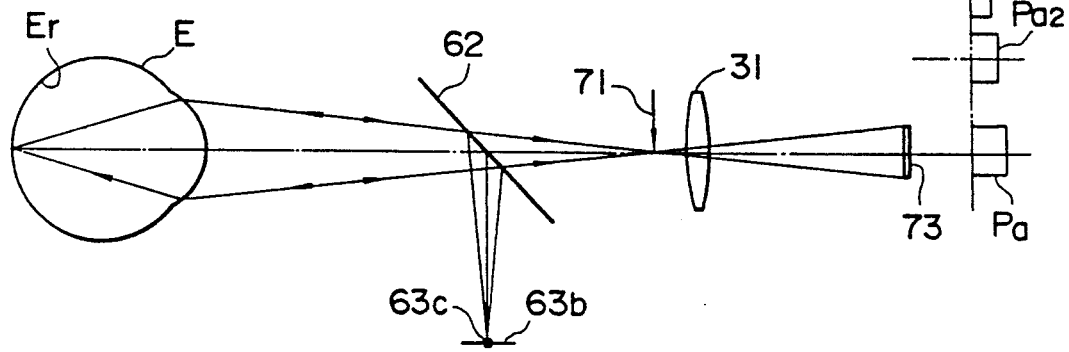
FIG. 4(A) through 4(C) are diagrammatic views showing the relation between an eye refraction and slit images, and the distribution of the quantity of light of a light receiving element.
Figure 4B:
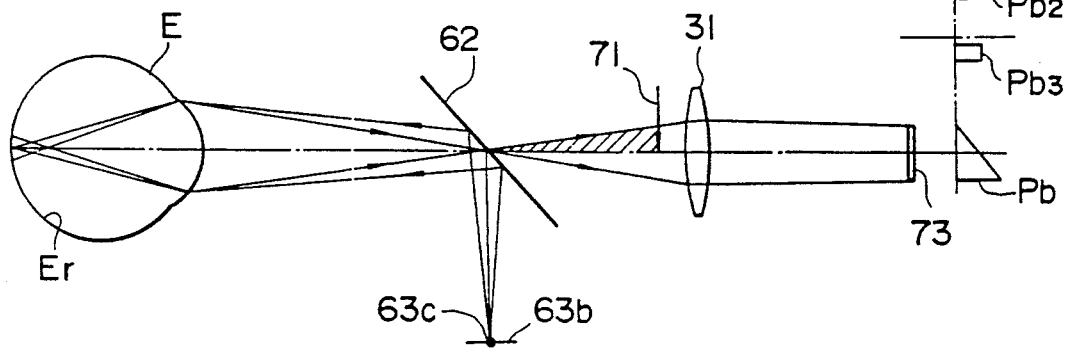
Figure 4C:
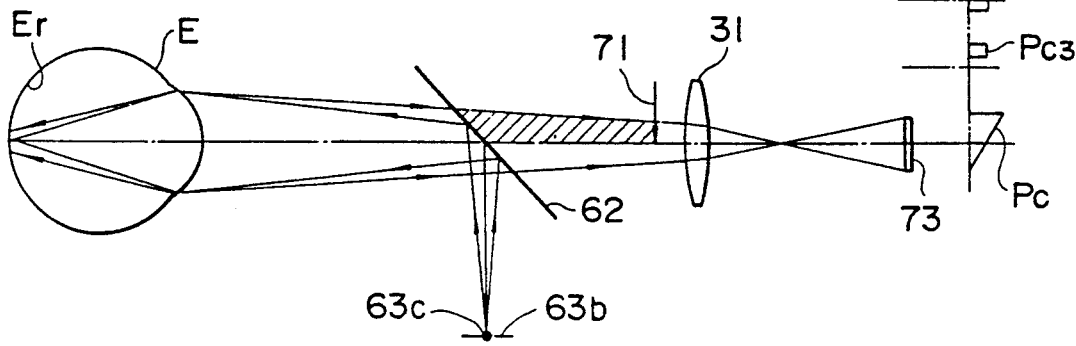

FIGS. 4(a) through 4(c) are diagrammatic views showing fluxes of light projected from a point light source 63c of the center of the surface light source 63b formed by the slit aperture 63a, and reflection fluxes of light from the center of the fundus Er. And a half mirror 62 is expediently disposed in front of an objective lens 31.

The refraction of an eye E to be tested in FIG. 4(a) is normal, so that an image of the point light source 63c is formed in focus on the fundus Er, and also is formed in focus on the shade member 71. $Pa_1$ in FIG. 4(a) shows the distribution of the quantity of light of an image of the pupil formed on the light receiving element 73, since the fluxes of light source is not obstructed by the shade member 71.

All fluxes of light from the lower side of the fundus Er (or the lower side of the axis) are obstructed (not shown) by the shade member, so that the distribution of the quantity of light on the light receiving element 73 results in $Pa_3$. On the other hand, the fluxes of light from the upper side is not obstructed by the shade member 71, so that the distribution results in $Pa_2$. Therefore, the distribution of the sum total of the fluxes on the light receiving element 73 becomes uniform as in Pa.

FIG. 4(B) shows a refraction below the normal of an eye E to be tested. In this case, an image of a point light source is formed out of focus in front of the shade member 71, and a part of fluxes of light of the image is obstructed by the shade member 71. And the distribution of the quantity of light of the image of the pupil formed on the light receiving element 73 results in $Pb_1$ in FIG. 4(B). That is, the $Pb_1$ is the distribution of the quantity of light formed on the light receiving element by the point light source 63c. And $Pb_3$ is the distribution of the quantity of light on the light receiving element 73 by the fluxes from the lower side of the fundus Er, $Pb_2$ being the distribution of the quantity of light on the light receiving element 73 by the fluxes from the upper side of the fundus Er.

The width x of the fluxes linearly changes according to the position of the spot light source on the fundus Er. In other words, the width x of the distribution of the fluxes formed on the light receiving element 73 becomes narrower according as the position of the point light source on the fundus Er moves up from the optical axis. On the contrary, the width x becomes broader as the position moves lower from the axis. Therefore, the distribution of the sum total of the quantity of light is slanted, as shown in Pb, as a result of its integration.

FIG. 4(c) shows a refraction over the normal of an eye to be tested. In this case, an image of a point light source is formed out of focus in the rear of the shade member 71, and a part of the fluxes of the image of the point light source is obstructed by the shade member 71.

$Pc_1$ in FIG. 4(c) shows the distribution of the quantity of light of the image of the pupil formed on the light receiving element 73.

$Pc_3$ shows the distribution of the fluxes on the light receiving element 7 by the fluxes (not shown) from the lower side of the fundus Er, $Pc_2$ showing the distribution on the element 7 by the fluxes from the upper side. The distribution of the sum total of light on the light receiving element 73, the same as in the above case, is slanted as shown in Pc.

Thus, the refraction of an eye E to be tested changes the fluxes obstructed by the shade member 71, and it produces various distributions of the quantity of light of the image of the pupil formed on the light receiving element 73, and the slant of the distribution of the quantity of light becomes sharper as the refraction deviates from the normal refraction. A measuring means 80 calculates the refraction based on the slant of the distribution of the quantity of light.

Japanese Patent Application Hei 1-24491 applied previously describes the principle that the refraction of an eye changes the slant of the distribution of the quantity of light on the light receiving element 73.

The miniaturization of a microscope for an operation can be achieved since a part of the axes is in common among the illuminating optical system 50, the projecting optical system, and the receiving optical system in the above embodiment. This miniaturization makes it possible to lengthen the working distance between the objective lens 31 and the eye E to be tested, so that the operation can easily be carried out. And furthermore, the miniaturization makes it possible to shorten the operating distance between the eyepiece 36 and the eye E to be tested, so that an operator can observe the eye E in a free posture. The alignment accuracy is permitted to be rough, because a photorefraction meter for measuring the refraction of an eye E to be tested is applied based on the slant of the distribution of the quantity of light projected on the light receiving element.

Figure 5:
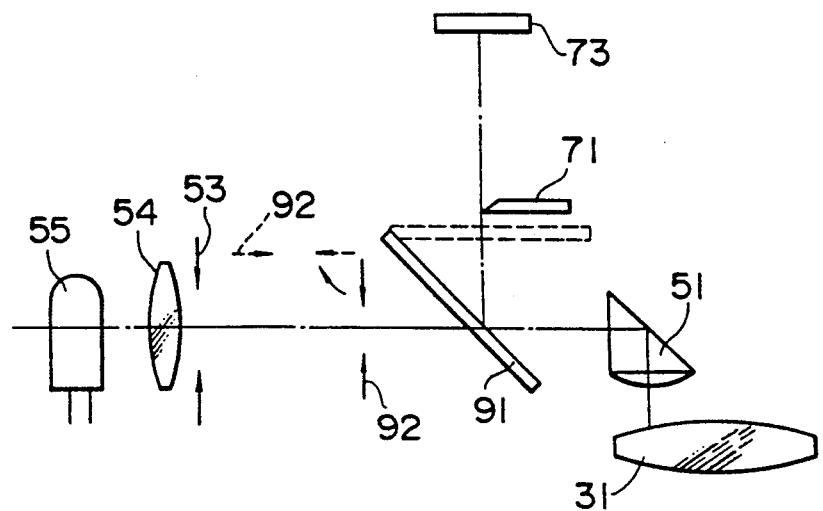
FIG. 5 is a schematic view showing another embodiment of the present invention.
Figure 6:
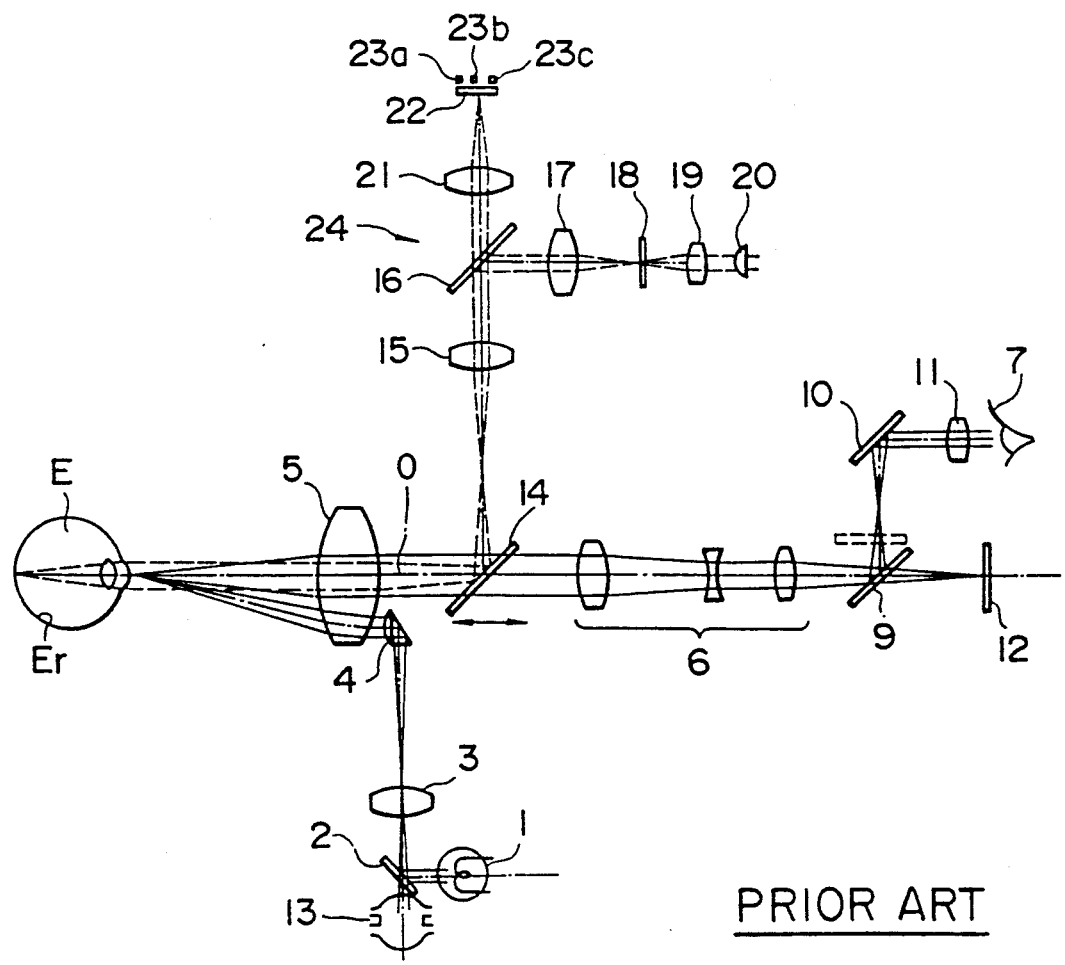
FIG. 6 is a schematic view showing construction of a optical system of the conventional microscope for an operation.
Figure 7:
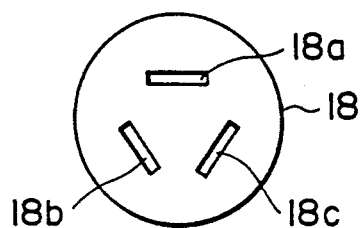
FIG. 7 is a plan view showing a projecting chart.
Figure 8:
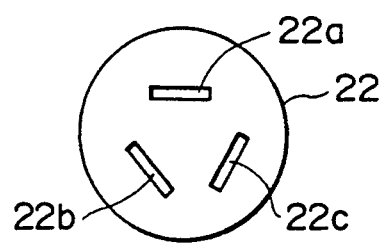
FIG. 8 is a plan view showing a light receiving chart.

FIG. 5 is another embodiment where the light source of the illuminating optical system 50 shares that of the projecting optical system.

Referring to FIG. 5, the numeral 91 designates a half mirror, which is moved to the position shown as the stitch line in observing the fundus Er, and is inserted into the position shown as the continuous line on the optical path in measuring the refraction. The slit plate 92 is, the same as the half mirror 91, moved to the position of the stitch line in observing the fundus Er, and is inserted into the position shown as the continuous line on the optical path in measuring the refraction.

What is claimed is:

1. An operation microscope, comprising:

an illuminating optical system for illuminating an eye;
an observing optical system for observing said eye;
a projecting optical system for projecting measuring light fluxes onto the fundus of said eye;
a receiving optical system for receiving at least a portion of the measuring light fluxes reflected from said fundus including a shading member for obstructing a part of the measuring light fluxes reflected from said fundus, a light receiving element disposed at a position conjugate with the pupil of said eye for receiving the measuring light fluxes partly obstructed by said shading member, and a measuring means for measuring the refraction of the eye based on the distribution of the quantity of measuring light fluxes received by said light receiving element;
said illuminating optical system, and projecting optical system and said receiving optical system each having a respective optical axis, each of said axes having at least a portion which is common to the axes of the remaining two; and
said measuring means measuring the refraction of the eye based on a slant of the distribution of the quantity of measuring light fluxes received by said light receiving element.

2. An operation microscope, comprising:
an illuminating optical system for illuminating an eye;
an observing optical system for observing said eye;
a projecting optical system for projecting measuring light fluxes onto the fundus of said eye;
a receiving optical system for receiving at least a portion of the measuring light fluxes reflected from said fundus including a shading member for obstructing a part of the measuring light fluxes reflected from said fundus dependent upon the refraction of the eye, a light receiving element disposed at a position conjugate with the pupil of said eye for receiving an unobstructed portion of the measuring light fluxes, and a measuring means for measuring the refraction of the eye based on the distribution of the quantity of measuring light fluxes received by said light receiving element; and
said projecting optical system and said receiving optical system having respective optical axes, each of said axes having at least a portion which is common to the other axis.

3. An operation microscope according to claim 2, wherein said illuminating optical system and said projecting optical system have a common light source.

4. An operation microscope according to claim 3, wherein illuminating light of said illuminating optical system is visible light and measuring light fluxes of said projecting optical system are infrared rays.

5. An operation microscope according to claim 2, wherein illuminating light of said illuminating optical system is visible light and the measuring light fluxes of said projecting optical system are infrared rays.

6. An operation microscope according to claim 2, wherein a dichroic mirror is provided within an optical axis of said illuminating optical system, the measuring light fluxes of said projecting optical system are reflected from said dichroic mirror and then are projected onto the fundus of said eye, the reflected measuring light fluxes from said fundus are projected onto said dichroic mirror and the reflected measuring light fluxes from the dichroic mirror then are received by said light receiving element, and the illuminating light of said illuminating optical system passes through said dichroic mirror and then illuminates said eye.

7. An operation microscope according to claim 6, wherein the illuminating light of said illuminating optical system is visible light and the measuring light fluxes of said projecting optical system are infrared rays.

8. An operation microscope according to claim 6, wherein said illuminating optical system and said projecting optical system have a common light source.

* * * * *